United States Patent [19]

Saxton et al.

[11] Patent Number: 5,241,118
[45] Date of Patent: Aug. 31, 1993

[54] PROCESS FOR THE PREPARATION OF TRISUBSTITUTED UREAS BY REDUCTIVE CARBONYLATION

[75] Inventors: Robert J. Saxton; Wilfred P. Shum, both of West Chester; Edward T. Shawl, Wallingford; Haven S. Kesling, Jr., Drexel Hill; John G. Zajacek, Devon, all of Pa.

[73] Assignee: Arco Chemical Technology, L.P., Wilmington, Del.

[21] Appl. No.: 796,499

[22] Filed: Nov. 22, 1991

Related U.S. Application Data

[63] Continuation-in-part of Ser. No. 680,466, Apr. 4, 1991, abandoned.

[51] Int. Cl.$^5$ .......................................... C07C 275/76
[52] U.S. Cl. ........................................ 564/55; 560/344; 564/60; 564/61
[58] Field of Search ................ 564/48, 61, 55, 60; 560/344

[56] References Cited

U.S. PATENT DOCUMENTS

| | | | |
|---|---|---|---|
| 3,993,685 | 11/1976 | Zajacek et al. | 260/471 C |
| 4,052,454 | 10/1977 | Zajacek et al. | 260/553 A |
| 4,871,871 | 10/1989 | Shawl et al. | 560/344 |
| 4,873,364 | 10/1989 | Shawl et al. | 560/344 |
| 4,883,908 | 11/1989 | Shawl et al. | 560/344 |
| 5,099,021 | 3/1992 | Wörther et al. | 546/198 |

FOREIGN PATENT DOCUMENTS

| | | |
|---|---|---|
| 0250037 | 12/1987 | European Pat. Off. . |
| 0319111 | 6/1989 | European Pat. Off. . |
| 2333973A | 7/1989 | United Kingdom . |
| 2233973 | 7/1991 | United Kingdom . |

OTHER PUBLICATIONS

J. Org. Chem. 40 (1975) 2819.
Helv. Chim. Acta. 55 (1972).
Chem. Abstracts 90 22659g (Swiss Patent No. 605,699) (1979).
J. Mol. Catal. 59 (1990) L15.
J. Organometal. Chem. 290 (1985) 249.
Chem. Abstracts 104 224726v (East German Patent No. 227,700) (1986).
West German Patent No. 3,405,582 (Chem. Abstracts 102 78596t) (1985).
Chem. Abstracts 91 20147k (West German Patent No. 2,742,158) (1975).
J. Org. Chem. 53 (1988) 1243.

Primary Examiner—Glennon H. Hollrah
Attorney, Agent, or Firm—Jonathan L. Schuchardt

[57] ABSTRACT

A process for preparing trisubstituted ureas is disclosed. A nitroarene is reacted with carbon monoxide and a secondary amine in the presence of a Group VIII transition metal catalyst and optionally one or more promoters selected from primary amines, halide ion-containing compounds, and chelating phosphorus and nitrogen compounds.

25 Claims, No Drawings

PROCESS FOR THE PREPARATION OF TRISUBSTITUTED UREAS BY REDUCTIVE CARBONYLATION

This application is a continuation-in-part of co-pending application Ser. No. 07/680,466, filed Apr. 4, 1991 (now abandoned).

FIELD OF THE INVENTION

The invention relates to the field of urea synthesis. More specifically, a process is disclosed for preparing trisubstituted ureas by reductive carbonylation of a nitroarene in the presence of a secondary amine and a Group VIII transition metal catalyst. The ureas are useful precursors to aromatic isocyanates.

BACKGROUND OF THE INVENTION

Reductive carbonylation of nitroarenes and/or arylamines in the presence of various catalysts is an effective strategy for preparing N,N'-diarylureas. For example, Heck et al. (J. Org. Chem. 40 (1975) 2819) describe the synthesis of various symmetric diarylureas from the reaction of nitroarenes, aromatic amines, and carbon monoxide in the presence of a palladium catalyst. The authors also note, however, that complicated mixtures of ureas result when aromatic amines and nitroarenes containing different substituents react in this process. For example, the reaction of aniline with p-chloronitrobenzene gives N,N'-diphenylurea and N,N'-bis(p-chlorophenyl)urea in addition to the expected Nphenyl-N'-(p-chlorophenyl)urea.

Similarly, Watanabe et al. (J. Organometal. Chem. 290 (1985) 249) reported that n-butylamine reacts with nitrobenzene and carbon monoxide in the presence of a platinum compound to give a mixture of N,N'-dibutylurea (46%), N-butyl-N'-phenylurea (46%), and N,N'-diphenylurea (6%).

UK Patent Application GB 2 233 973A teaches a process in which a primary aliphatic amine reacts with a nitroarene and carbon monoxide in the presence of a rhodium catalyst to give only the symmetric N,N'-dialkylurea and a primary aromatic amine. No unsymmetric urea is produced. When a secondary aliphatic amine is used in place of the primary aliphatic amine, only traces of urea products are detected.

East German Patent No. 227,700 (Chem. Abstracts 104 224726v) teaches to prepare N,N-dimethyl-N'-phenylurea from nitrobenzene, CO, and dimethylamine in the presence of a sulfur/vanadium pentoxide catalyst system. The reference teaches the criticality of the vanadium pentoxide, and does not suggest using a Group VIII metal catalyst for the process.

The references discussed in the preceding paragraphs make it clear that a synthesis of an unsymmetric urea from a nitroarene and a secondary amine using a Group VIII transition metal catalyst is likely to give, if anything, a complicated mixture of urea products. On the other hand, a selective process for producing trisubstituted ureas, especially N'-aryl-N,N-dialkylureas, is desirable because these ureas are easily cracked in the presence of various promoters to give aryl isocyanates.

SUMMARY OF THE INVENTION

The present invention is a process for preparing a trisubstituted urea. The process comprises reacting a nitroarene with carbon monoxide and a secondary amine in the presence of a Group VIII transition metal catalyst to produce the trisubstituted urea. The reaction is optionally performed in the presence of one or more promoters selected from primary amines, halide ion-containing compounds, and chelating phosphorus and nitrogen compounds. High yields of trisubstituted ureas are obtained under optimum conditions.

DETAILED DESCRIPTION OF THE INVENTION

In the process of the invention, a nitroarene is reacted with carbon monoxide and a secondary amine in the presence of a Group VIII transition metal compound.

The nitroarene may be any aromatic compound having one or more nitro substituents. The aromatic ring or rings may be substituted with one or more additional substituents selected from the group consisting of amino, halogen, alkoxy, and $C_1$–$C_{10}$ alkyl. Examples of suitable nitroarenes include, but are not limited to, nitrobenzene, nitrotoluenes, nitronaphthalenes, dinitrotoluenes, nitrochlorobenzenes, nitroanisoles, nitrotoluidines, bis(nitrophenyl) ethers, bis(nitrophenyl)alkylenes, nitro-substituted biphenyls, and the like, and mixtures thereof.

Secondary amines useful in the process of the invention have the general formula HNRR', in which R and R', which may be the same or different, are aryl, aralkyl, or alkyl groups having from 1 to 30 carbons. For example, R and R' may both be alkyl or cycloalkyl groups, as in dimethylamine, diethylamine, di-n-butylamine, methyl-n-butylamine, ethylcyclohexylamine, N,N-dicyclohexylamine, and the like. Alternatively, R and R' may both be aryl groups, as in diphenylamine. Mixed aryl-alkyl amines, such as N-methylaniline, N-cyclohexylaniline, and N-cyclohexylbenzylamine, and the like, are suitable. R and R' may also form a ring. Cyclic secondary amines such as piperidine, pyrrolidine, and the like, and cyclic secondary amines that contain heteroatoms, such as morpholine and substituted morpholines, are suitable. Mixtures of secondary amines may be used. Preferred secondary amines, for reasons of availability and effectiveness, are aliphatic amines such as dimethylamine, diethylamine, and the like.

Any amount of secondary amine may be employed. For economic reasons, it is preferred to use an amount less than about 5 equivalents of secondary amine per nitro group equivalent. More preferably, an amount of secondary amine within the range of about 0.5 to 2.0 equivalents per nitro group equivalent is used.

The Group VIII transition metal catalysts of the invention are transition metal compounds containing iron, cobalt, nickel, ruthenium, rhodium, palladium, osmium, iridium, or platinum. The metal may be present in supported or unsupported elemental form, or in the form of a salt or other transition metal complex containing the metal. Carbonyls, halides, oxides, sulfates, nitrates, acetates, and other transition metal salts may be used provided that at least one Group VIII metal is present. Mixtures of various Group VIII metal compounds may be used. Bimetallic and poly-metallic compounds may also be used provided that at least one Group VIII transition metal compound is present. Examples of suitable Group VIII transition metal compounds include, but are not limited to, triruthenium dodecacarbonyl, ruthenium trichloride, ruthenium oxide, triosmium dodecacarbonyl, platinum(II) chloride, platinum(IV) chloride, platinum black, platinum on alumina, platinum(IV) oxide, palladium, palladium(II)

acetate, palladium(II) nitrate hydrate, bis(triphenylphosphine)palladium(II) chloride, cobalt(II) chloride hexahydrate, cobalt oxide, cobalt(II) sulfate hydrate, iron pentacarbonyl, iron(II) sulfate heptahydrate, and the like, and mixtures thereof.

Optionally, the process of the invention is performed in the presence of one or more reaction promoters selected from the group consisting of primary amines, halide ion-containing compounds, and chelating phosphorus and nitrogen compounds. Examples of suitable amines include methylamine, ethylamine, aniline, ethylene diamine, n-butylamine, isopropylamine, and the like, and mixtures thereof. In place of a primary amine it is also possible to use any source of reducing equivalents, such as water, hydrogen, compounds containing active hydrogens (alcohols, amines, carboxylic acids, thiols), and redox metals. Suitable halide ion-containing compounds include any source of fluoride, chloride, bromide, or iodide. Examples of suitable halide ioncontaining compounds include tetraalkylammonium halides, alkali metal halide salts, alkaline earth metal halide salts, iminium halide salts, and the like, and mixtures thereof. Preferably, either a primary amine or a halide ion-containing promoter is used in the process of the invention. More preferably, both are used together.

Suitable promoters also include chelating nitrogen and phosphorus compounds. Examples of suitable chelating N and P compounds include, but are not limited to bis(diphenylphosphino)methane, bis(diphenylphosphino)propane, 2,2'-bipyridine, 1,10-phenanthroline, 2,9-dimethylphenanthroline, 4,7-diphenylphenanthroline, 3,4,7,7-tetramethylphenanthroline, and the like, and mixtures thereof. Compounds having the general formula

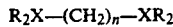

$$R_2X-(CH_2)_n-XR_2$$

in which R is an alkyl or aryl group, X is phosphorus or nitrogen, and n is an integer from 1 to 10 are generally suitable.

Any desired amount of primary amine, halide ion containing compound, or phosphorus/nitrogen chelating compound may be used in the process of the invention. Generally, it is preferred to use an amount within the range of about 0.1 to 10 equivalents of promoter per equivalent of transition metal compound employed. More preferably, an amount within the range of about 0.5 to 5 equivalents of promoter is used.

The process of the invention may be performed at any desired temperature. Preferably, the process is performed at a temperature within the range of about 40° C. to about 250° C. More preferred is the range from about 90° C. to about 200° C. Trisubstituted ureas that are substantially free of by-products can be prepared at temperatures within the range of about 90° C. to about 200° C. A particularly preferred temperature range is from about 100° C. to about 170° C. At temperatures below about 40° C., the reaction is ordinarily too slow to be useful. At temperatures greater than about 250° C., yields of the desired trisubstituted ureas are diminished at the expense of various side products.

Interestingly, N,N-dialkyl-N',N'-dialkylureas (bis(dialkylureas)) are absent from the product mixture when a dialkyl amine is reacted with a nitroarene according to the process of this invention. This result is surprising in view of the observation by Watanabe (*J. Organometal. Chem.* 290 (1985) 252) that N,N'-dibutylurea is a major product in the reaction of nitrobenzene with n-butylamine.

The process of the invention is performed under an atmosphere of carbon monoxide at pressures within the range of about 1 atmosphere to about 500 atmospheres. Preferably, the process is performed at pressures within the range of about 10 atm. to 170 atm. The reactor atmosphere optionally may include a percentage of inert gas, such as nitrogen, helium, argon, carbon dioxide, or the like.

The process of the invention is optionally performed in the presence of an inert organic solvent. Suitable solvents include, but are not limited to: aromatic hydrocarbons; alkyl-substituted aromatic hydrocarbons; linear, branched, and cyclic alkanes having up to 20 carbons; halogenated and nitrated aromatic and aliphatic hydrocarbons; and aromatic and aliphatic ethers, tertiary amines, sulfones, sulfoxides, nitriles, esters, and ketones. Specific examples of such solvents include benzene, toluene, xylenes, mesitylene, tetrahydronaphthalene, n-hexane, n-heptane, octane, nonane, cyclohexane, dodecane, octadecane, 2-methylhexane, dichloromethane, carbon tetrachloride, 1,2-dichloroethane, diphenyl ether, tetrahydrofuran, dibutyl ether, triethylamine, pyridine, dimethyl sulfoxide, sulfolane, methyl sulfone, propylene glycol dimethyl ether, ethyl acetate, methyl benzoate, acetone, acetophenone, acetonitrile, benzonitrile, and the like, and mixtures thereof.

The process of the invention may be performed in any suitable reactor. Preferably, the reactor is equipped with a means for controlling temperature and an agitating means. Heating and cooling means may be applied either internally or externally as desired to maintain the reactor temperature within the desired range.

The process of the invention may be performed batchwise or continuously, as desired. In a typical batch process, for example, the nitroarene, solvent, secondary amine, transition metal catalyst, and any optional promoters are charged to the reactor and heated to the desired reaction temperature under an atmosphere of carbon monoxide, and optionally an inert gas. If desired, a solution containing the catalyst can be introduced following combination and heating of the other reactants. Alternatively, any of the substrates can be added to a mixture that contains the catalyst.

The trisubstituted urea product may be recovered from the reaction mixture by any suitable method, including, for example, filtration, distillation, extraction, and the like.

In a preferred embodiment of the invention, the unsymmetric urea product is heated in the vapor phase or while dissolved or slurried in an inert organic solvent, optionally in the presence of one or more reaction promoters, to produce an aryl isocyanate. Such a process, which is known in the art as cracking, is described in U.S. Pat. Nos. 4,871,871, 4,873,364, and 4,883,908. The teachings of these patents are incorporated herein by reference. Any of the promoters known in the art may be used. Preferred promoters include, but are not limited to, mineral acids, amine halide salts, sulfonic acids, and the like.

The following examples merely illustrate the invention. Those skilled in the art will recognize numerous variations that are within the spirit of the invention and scope of the claims.

EXAMPLES 1-18

Preparation of N'-Phenyl-N,N-diethylurea

General Procedure

A 300-mL autoclave reactor was charged with nitrobenzene (8.1 g), diethylamine (1-5 equivalents), aniline (0-1 equivalents), solvent (90 mL), triruthenium dodecacarbonyl (0.39 g), and chloride ion-containing promoter (1-5 equivalents based on the amount of Ru catalyst). Carbon monoxide (60 atm) was added, and the contents were heated to the desired reaction temperature with stirring. Carbon monoxide was periodically added to replenish any that was consumed in the reaction. After the desired reaction time, the reaction products were analyzed by gas chromatography and high-performance liquid chromatography to determine the percent conversion of nitrobenzene and the selectivity to various reaction products.

The desired product was the unsymmetric urea, N'-phenyl-N,N-diethylurea (DEPU). Other products observed were N,N'-diphenylurea (DPU), N-ethylaniline (EA), and N-ethylformanilide (EF). The halide ion-containing compound used as a reaction promoter was bis(triphenylphosphine)iminium chloride (PPNCl) in all cases except for Example 4, in which tetraethylammonium chloride (TEAC) was used.

The effect of using various reaction promoters is illustrated in Table 1:

TABLE 1

Synthesis of N'-Phenyl-N,N-diethylurea by Carbonylation
Effect of Promoters[4]

| Ex | Temp (°C.) | Time (h) | Aniline[2] (eq) | Cl-cpd[3] (eq) | Conv. (%) | Selectivity[1] (%) DEPU | DPU | Net % aniline |
|---|---|---|---|---|---|---|---|---|
| 1 | 140 | 2.0 | 0 | 0 | 30 | 10 | — | 63 |
| 2 | 140 | 1.0 | 0 | 5.0 | 41 | 40 | 4.5 | 34 |
| 3 | 140 | 1.0 | 1.0 | 0 | 43 | 22 | 2.2 | 17 |
| 4 | 140 | 0.5 | 1.0 | 5.0 | 98 | 62 | 13 | −6.2 |
| 5 | 140 | 0.5 | 1.0 | 5.0 | 99 | 73 | 22 | −4.2 |
| 6 | 140 | 1.0 | 1.0 | 1.0 | 79 | 59 | 7 | 6.1 |

[1]Products: DEPU = N'-phenyl-N,N-diethylurea; DPU = N,N'-diphenylurea;
[2]Eq. aniline charged/eq. nitrobenzene
[3]Chloride-containing promoter was bis(triphenylphosphine)iminium chloride in Examples 1-3, 5, and 6; tetraethylammonium chloride was used for Example 4. Equivalent amount calculated/Ru$_3$(CO)$_{12}$ eq.
[4]Diethylamine (2 eq./eq. nitrobenzene) was used in each example, and all runs were performed in p-xylene solvent.

As shown in Table 1, the desired unsymmetric urea DEPU can be prepared without adding either a primary amine or a halidecontaining promoter (Example 1); most of the charged nitrobenzene was reduced to aniline. When both aniline and a chloride ion source (TEAC) were used, conversion was 98%, and selectivity to DEPU and 62%. With only a chloride source (Example 2), conversion after 1 hour was 41% and selectivity to DEPU was 40%. When only aniline was used as a promoter (Example 3), conversion was 43% and selectivity to DPU was 22%. With aniline present and bis(triphenylphosphine)iminium chloride (PPNCl) as the halide source, 99% conversion and 73% selectivity to DEPU were achieved. (Example 5).

TABLE 2

Synthesis of N'-Phenyl-N,N-diethylurea by Carbonylation
Effect of Temperature[2]

| Ex | Temp (°C.) | Time (h) | Conv. (%) | Selectivity[1] (%) DEPU | DPU | EA | EF | Net % Aniline |
|---|---|---|---|---|---|---|---|---|
| 5 | 140 | 0.5 | 99 | 73 | 22 | — | — | −4.2 |
| 7 | 110 | 1.0 | 40 | 49 | 2.2 | — | — | 10 |
| 8 | 170 | 0.5 | 99 | 30 | — | 40 | 40 | — |

[1]Products: DEPU = N'-phenyl-N,N-diethylurea; DPU = N,N'-diphenylurea; EA = N-ethylaniline; EF = N-ethylformanilide
[2]All reactions were performed with 2 eq. diethylamine/eq. nitrobenzene, 1 eq. aniline/eq. nitrobenzene, and 5 eq. bis(triphenylphosphine)iminium chloride/eq. Ru$_3$(CO)$_{12}$, using p-xylene as a solvent.

The effect of reaction temperature is illustrated in Table 2. At 140° C. (Example 5), conversion was nearly quantitative within 30 minutes, and selectivity to DEPU was high (73%). Decreasing the temperature to 110° C. (Example 7) resulted in incomplete conversion (40%) of the nitrobenzene after one hour. At 170° C., conversion was complete within 30 minutes, but selectivity to DEPU decreased; two new products, N-ethylaniline and N-ethylcarbanilide, were formed.

TABLE 3

Synthesis of N'-Phenyl-N,N-diethylurea by Carbonylation
Effect of Solvent[2]

| Ex | Temp (°C.) | Time (h) | Solvent | Conv. (%) | Selectivity[1] (%) DEPU | DPU | Net % Aniline |
|---|---|---|---|---|---|---|---|
| 5 | 140 | 0.5 | p-xylene | 99 | 73 | 22 | −4.2 |
| 9 | 140 | 0.5 | tetrahydrofuran | 99 | 83 | 9.4 | 2.8 |
| 10 | 140 | 0.5 | 1,4-dioxane | 85 | 65 | 4.1 | 17 |
| 11 | 140 | 0.5 | acetonitrile | 81 | 77 | 3.8 | 13 |
| 12 | 140 | 0.5 | o-dichlorobenzene | 99 | 63 | 13 | 6.5 |

[1]Products: DEPU = N,N-diethyl-N'-phenylurea; DPU = N,N'-diphenylurea
[2]All reactions were performed with 2 eq. dithylamine/eq. nitrobenzene, 1 eq. aniline/eq. nitrobenzene, and 5 eq. bis(triphenylphosphine)iminium chloride/eq. Ru$_3$(CO)$_{12}$.

The process of the invention may be performed in a wide range of solvents. As shown in Table 3, aromatic hydrocarbons, ethers, nitriles, and halogenated aromatic hydrocarbons are all suitable.

TABLE 4

Synthesis of N'-Phenyl-N,N-diethylurea by Carbonylation
Effect of Amount of Aniline Charged[2]

| Ex | Temp (°C.) | Time (h) | Aniline charged (eq/eq NO$_2$) | Conv (%) | Selectivity[1] (%) DEPU | DPU | Net % Aniline |
|---|---|---|---|---|---|---|---|
| 13 | 140 | 0.5 | 0 | 82 | 47 | 3.6 | 9.1 |
| 14 | 140 | 0.5 | 0.5 | 91 | 77 | 10 | 8.8 |
| 5 | 140 | 0.5 | 1.0 | 99 | 73 | 22 | −4.2 |

[1]Products: DEPU = N,N-diethyl-N'-phenylurea; DPU = N,N'-diphenylurea
[2]All reactions were performed with 2 eq. diethylamine/eq. nitrobenzene and 5 eq. bis(triphenylphosphine)iminium chloride/eq. Ru$_3$(CO)$_{12}$ using p-xylene as the solvent.

As discussed previously, conversion and selectivity to the unsymmetric urea can be improved by including a primary amine such as aniline in the process of the invention. Table 4 illustrates the effect of changing the amount of aniline used. Incomplete conversion was observed when aniline was omitted (Example 13). With one equivalent of aniline (Example 5), conversion was complete within 30 minutes, and selectivity to DEPU was 73%. With 0.5 equivalents of aniline (Example 14), conversion after 30 minutes was 91%, and selectivity was 77%.

TABLE 5

Synthesis of N'-Phenyl-N,N-diethylurea by Carbonylation
Effect of Amount of Diethylamine[2]

| Ex | Temp (°C.) | Time (h) | DEA (eq) | Solvent | Conv. (%) | Selectivity[1] (%) DEPU | DPU | Net % Aniline |
|---|---|---|---|---|---|---|---|---|
| 15 | 140 | 0.25 | 1.0 | THF | 92 | 91 | 5.7 | −1.2 |
| 9 | 140 | 0.50 | 2.0 | THF | 99 | 83 | 9.4 | 2.8 |
| 16 | 140 | 2.0 | 5.0 | p-xylene | 84 | 49 | 7.8 | 19 |

[1]Products: DEPU = N,N-diethyl-N'-phenylurea; DPU = N,N'-diphenylurea
[2]All reactions were performed with 1 eq. aniline/eq. nitrobenzene, and 5 eq. bis(triphenylphosphine)iminium chloride/eq. $Ru_3(CO)_{12}$.

As shown in Table 5, the proportion of diethylamine used also impacts the selectivity to DEPU. With 5 equivalents of DEA (Example 16), 49% selectivity to DEPU was observed, and there was a large increase in the amount of aniline produced. With 1-2 equivalents of DEA (Examples 9, 15), good conversions (92-99%) and high selectivities to DEPU (83-91%) were achieved.

TABLE 6

Synthesis of N'-Phenyl-N,N-diethylurea by Carbonylation
Effect of Group VIII Metal

| Ex | Catalyst | Time (h) | Conv. (%) | Selectivity (%) DEPU | DPU | Net % Aniline |
|---|---|---|---|---|---|---|
| 15 | $Ru_3(CO)_{12}$ | 0.25 | 92 | 91 | 5.7 | −1.2 |
| 17 | $PdCl_2(PPh_3)_2$ | 1.0 | 18 | 65 | 7.8 | 11.1 |
| 18 | $RhCl(PPh_3)_3$ | 1.0 | 1.5 | 90 | 8.0 | 0.5 |

[1]Products: DEPU = N,N-diethyl-N'-phenylurea; DPU = N,N'-diphenylurea
[2]All reactions were performed in THF at 140° C. and 60 atm. CO with 0.5 eq. aniline/eq. nitrobenzene. Substrate/catalyst = 100. TPPCl (5 eq./eq. catalyst) was used in Example 15 only.

Table 6 shows how other Group VIII metals can be used as catalysts for the process of the invention. Table 7 illustrates the carbonylation reaction for various nitroarenes.

TABLE 7

Nitroarene Carbonylation

| Ex | Substrate | Time (h) | Conv. (%) | Products (%) |
|---|---|---|---|---|
| 15 | Nitrobenzene | 0.25 | 92 | DEPU (91%), DPU (5.7%) |
| 19 | 4,4'-dinitrodiphenylmethane | 0.50 | 83 | MBPDEU (21%) |
| 20 | 4,4'-dinitrobiphenyl | 1.0 | 40 | BPDEU (60%) |

[1]Products: DEPU = N,N-diethyl-N'-phenylurea; DPU = N,N'-diphenylurea MBPDEU = 4,4'-methylene-bis-(N'-phenyl-N,N-diethylurea) BPDEU = 4,4'-bis-(N'-phenyl-N,N-diethylurea)
[2]All reactions were performed in THF at 140° C. and 60 atm. CO with 0.5 eq. aniline/eq. substrate using triruthenium dodecacarbonyl as the catalyst. Substrate/catalyst/TPPCl = 100/5/1. One eq. of diethylamine/eq. substrate was used.

EXAMPLE 19

Preparation of N'-Phenyl-N,N-pyrrolidinylurea

The procedure of Examples 1-18 was generally followed with nitrobenzene (8.1 g), pyrrolidine (1 eq.), triruthenium dodecacarbonyl (0.39 g), aniline (1 eq.), bis(triphenylphosphine) iminium chloride (5 eq based on catalyst), and tetrahydrofuran (90 mL). After 30 minutes at 140° C., conversion of nitrobenzene was 97%. The products obtained were N'-phenyl-N,N-pyrrolidinylurea (49%), N,N'-diphenylurea (9%), and aniline (about 40%).

EXAMPLE 20

Carbonylation of 2,4-Dinitrotoluene in the presence of Diphenylamine

A 300-mL autoclave reactor was charged with 2,4-dinitrotoluene (6.45 g), N,N-diphenylamine (6.5 eq.), triruthenium dodecacarbonyl (0.39 g), bis(triphenylphosphine) iminium chloride (5 eq. based on catalyst), and tetrahydrofuran (90 mL). Carbon monoxide (60 atm.) was added, and the mixture was heated with stirring to 140° C. After 4 h, conversion of the 2,4-dinitrotoluene was 35%. The yield of toluene-2,4-bis(diphenylurea) was about 1-2%. Other products observed we nitrotoluidine isomers and nitrotoluene-mono-(diphenylurea) isomers.

EXAMPLE 21

Carbonylation of 2,4-Dinitrotoluene in the presence of Diethylamine

A 300-mL autoclave reactor was charged with o-dichlorobenzene (55 mL), triruthenium dodecacarbonyl (0.40 g, 0.63 mmol), bis(triphenylphosphine) iminium chloride (1.93 g, 3.36 mmol), and dodecane (1 g). After leak-testing and purging with nitrogen, the reactor was pressurized with carbon monoxide to 150 atmospheres. The mixture was stirred (1500 rpm) and heated to 140° C. A solution of o-dichlorobenzene (80 mL), 2,4-dinitrotoluene (10.5 g, 57.7 mmol) and diethylamine (21.7 g, 297 mmol) was pumped into the reactor at a rate of 20 mL/hour. The total reaction time at 140° C. was 16 h. After this time, the reactor was cooled to room temperature. Analysis showed complete conversion of 2,4-dinitrotoluene. The product composition was: 90% of toluene-2,4-bis(diethylurea), and 10% of 2-aminotoluene-4-(diethylurea).

We claim:

1. A process for making a trisubstituted urea, said process comprising:
   reacting a nitroarene with carbon monoxide and a secondary amine in the presence of a Group VIII transition metal catalyst and from about 0.1 to about 10 equivalents per equivalent of transition metal catalyst of a mixture of promoters which comprises a primary amine and a halide ion-containing compound to produce the trisubstituted urea.

2. The process of claim 1 wherein the nitroarene is selected from the group consisting of nitrobenzene, nitrotoluenes, nitrotoluidines, dinitrobenzenes, dinitrotoluenes, alkylated nitroarenes, bis(nitrophenyl) ethers, nitro-substituted biphenyls, and bis(nitrophenyl)alkylenes.

3. The process of claim 1 wherein the nitroarene is selected from the group consisting of nitrobenzene, nitrotoluenes, 2,4-dinitrotoluene, 2,6-dinitrotoluene, 4,4'-bis(nitrophenyl)methylene, 4,4'-bis(nitrophenyl) ether, 2,2-bis(4-nitrophenyl)propane, 1,1-bis(4-nitrophenyl)-1-phenylethane, nitro-substituted ethylbenzenes, and 4,4'-dinitrobiphenyl.

4. The process of claim 1 wherein the process is performed in the presence of a chelating phosphorus or nitrogen compound.

5. The process of claim 1 wherein the process is performed at a temperature within the range of about 40° C. to about 250° C.

6. The process of claim 1 wherein the process is performed in the presence of one or more organic solvents selected from the group consisting of aromatic hydrocarbons, alkyl-substituted aromatic hydrocarbons, alkanes, cycloalkanes, halogenated aliphatic and aromatic hydrocarbons, nitro compounds, tertiary amines, sulfones, sulfoxides, and aromatic and aliphatic ethers, ketones, esters, and nitriles.

7. The process of claim 1 wherein the process is performed at a pressure within the range of about 1 to about 500 atmospheres.

8. The process of claim 1 wherein the Group VIII transition metal catalyst is a ruthenium compound.

9. The process of claim 8 wherein the ruthenium compound is selected from the group consisting of triruthenium dodecacarbonyl, ruthenium trichloride, and ruthenium oxide.

10. The process of claim 9 wherein the process is performed in the presence of aniline and at least about one mole of halide ion-containing compound per mole of triruthenium dodecacarbonyl.

11. The process of claim 1 wherein the trisubstituted urea is heated in the vapor phase or in an organic solvent, optionally in the presence of a promoter, to thermally convert the trisubstituted urea to an aryl isocyanate.

12. A process for making a trisubstituted urea, said process comprising:
reacting a nitroarene selected from the group consisting of nitrobenzene, nitrotoluene, nitrotoluidines, dinitrobenzenes, dinitrotoluenes, bis(nitrophenyl) ethers, nitro-substituted biphenyls, and bis(nitrophenyl)alkylenes, with carbon monoxide and a secondary amine in the presence of a ruthenium compound and from about 0.1 to about 10 equivalents per equivalent of ruthenium compound of a mixture of promoters which comprises a primary amine and a halide ion-containing compound at a temperature within the range of about 40° C. to about 250° C. to produce the trisubstituted urea.

13. The process of claim 12 wherein the nitroarene is a dinitrotoluene, and the secondary amine is selected from the group consisting of dimethylamine, diethylamine, and diisopropylamine.

14. The process of claim 12 wherein the ruthenium compound is selected from the group consisting of triruthenium dodecacarbonyl, ruthenium trichloride, and ruthenium oxide.

15. The process of claim 12 wherein the process is performed in the presence of aniline and at least about one mole of a halide ion-containing compound per mole of ruthenium compound.

16. The process of claim 12 wherein the process is performed in the presence of a chelating nitrogen or phosphorus compound.

17. The process of claim 12 wherein the process is performed at a temperature within the range of about 90° C. to about 200° C.

18. The process of claim 12 wherein the process is performed at a pressure within the range of about 10 to about 170 atmospheres.

19. The process of claim 12 wherein the process is performed in the presence of one or more organic solvents selected from the group consisting of aromatic hydrocarbons, alkyl-substituted aromatic hydrocarbons, alkanes, cycloalkanes, halogenated aliphatic and aromatic hydrocarbons, nitro compounds, tertiary amines, sulfones, sulfoxides, and aromatic and aliphatic ethers, ketones, esters, and nitriles.

20. The process of claim 12 wherein the trisubstituted urea is heated in the vapor phase or in an organic solvent, optionally in the presence of a promoter, to thermally convert the trisubstituted urea to an aryl isocyanate.

21. A process for making a trisubstituted urea, said process comprising:
reacting a nitroarene with carbon monoxide and a secondary amine selected from the group consisting of dimethylamine and diethylamine in the presence of a ruthenium compound and from about 0.1 to about 10 equivalents per equivalent of ruthenium compound of a mixture of promoters which comprises a primary amine and a chloride ion-containing compound at a temperature within the range of about 90° C. to about 200° C. to produce the trisubstituted urea.

22. The process of claim 21 wherein the nitroarene is one or more dinitrotoluene isomers.

23. The process of claim 21 wherein the process is performed at a pressure within the range of about 10 to 170 atmospheres.

24. The process of claim 21 wherein the ruthenium compound is triruthenium dodecacarbonyl, and the chloride ion-containing compound is selected from the group consisting of bis(triphenylphosphine)iminium chloride and tetralkylammonium chloride compounds.

25. The process of claim 21 wherein the trisubstituted urea is heated in the vapor phase or in an organic solvent, optionally in the presence of a promoter, to thermally convert the trisubstituted urea to an aryl isocyanate.

* * * * *